US00PP14860P2

(12) United States Plant Patent
Fear et al.

(10) Patent No.: US PP14,860 P2
(45) Date of Patent: Jun. 1, 2004

(54) RASPBERRY PLANT NAMED 'DRISCOLL FRANCESCA'

(50) Latin Name: *Rubus idaeus L.*
Varietal Denomination: Driscoll Francesca

(75) Inventors: Carlos D. Fear, Aptos, CA (US); Richard E. Harrison, Aptos, CA (US); Fred M. Cook, Aptos, CA (US); Gavin Sills, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 3 days.

(21) Appl. No.: 10/306,458

(22) Filed: Nov. 27, 2002

(51) Int. Cl.[7] ..... A01H 5/00
(52) U.S. Cl. ..... Plt./204
(58) Field of Search ..... Plt./204

*Primary Examiner*—Anne Marie Grunberg
*Assistant Examiner*—Susan B. McCormick-Ewoldt
(74) *Attorney, Agent, or Firm*—Pennie & Edmonds LLP

(57) ABSTRACT

The present invention relates to a new and distinct cultivar of raspberry plant named Driscoll Francesca. The new cultivar is distinguished from other raspberry cultivars by its fruit firmness, fruit structure, yield and flavor. The new cultivar is distinguished from its seed parent by having better flavor, it is distinguished from its pollen parent by producing fruit of consistent shape and good firmness.

3 Drawing Sheets

Latin name of the genus and species of the plant claimed: The variety is botanically identified as *Rubus idaeus L.*

1. BACKGROUND OF THE INVENTION

The new cultivar of raspberry plant was developed from the hybridization of the selection 'Tola' (U.S. Plant Pat. No. 11,087) as the seed parent with the selection 'Isabel' (an unpatented variety) as the pollen parent. The parents were crossed in 1996; whereafter fruit and seed were collected to produce seedlings for field planting in Oxnard, Calif. in 1997. The new cultivar was selected from these seedlings in 1997 for its excellent fruit size and flavor. The new cultivar has been asexually propagated by in vitro shoot tip culture, root sucker division and root cuttings at the Cassin Ranch in Santa Cruz county, Calif. and has been shown to maintain the desired and distinguishing characteristics after propagation over several generations.

2. SUMMARY OF THE INVENTION

The present invention provides a new and distinct cultivar of red raspberry plant named 'Driscoll Francesca'. The cultivar is botanically identified as *Rubus idaeus L.* The 'Driscoll Francesca' red raspberry plant produces a primocane crop which begins in mid-July and continues until mid October. The floricane crop begins in mid-May and continues until late July. Both the primocane and floricane yields are high relative to other comparable varieties. The fruit of 'Driscoll Francesca' is notably quite firm and very consistent with regard to its size and shape throughout its harvest period and has good flavor. The fruit of 'Driscoll Francesca' separates easily from its receptacle.

3. BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics.

4. DETAILED BOTANICAL DESCRIPTION

Figure 1:
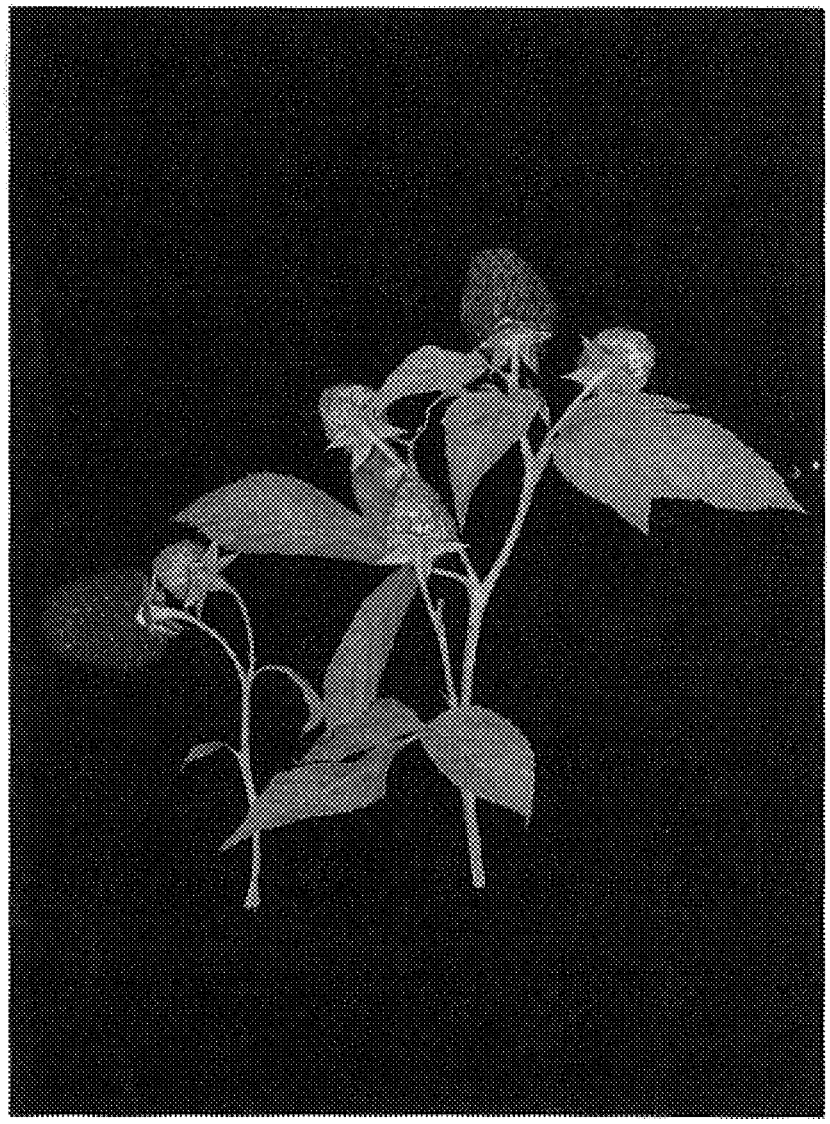
FIG. 1 is a photograph of 'Driscoll Francesca' primocane fruiting lateral showing ripe and unripe fruit.
Figure 2:
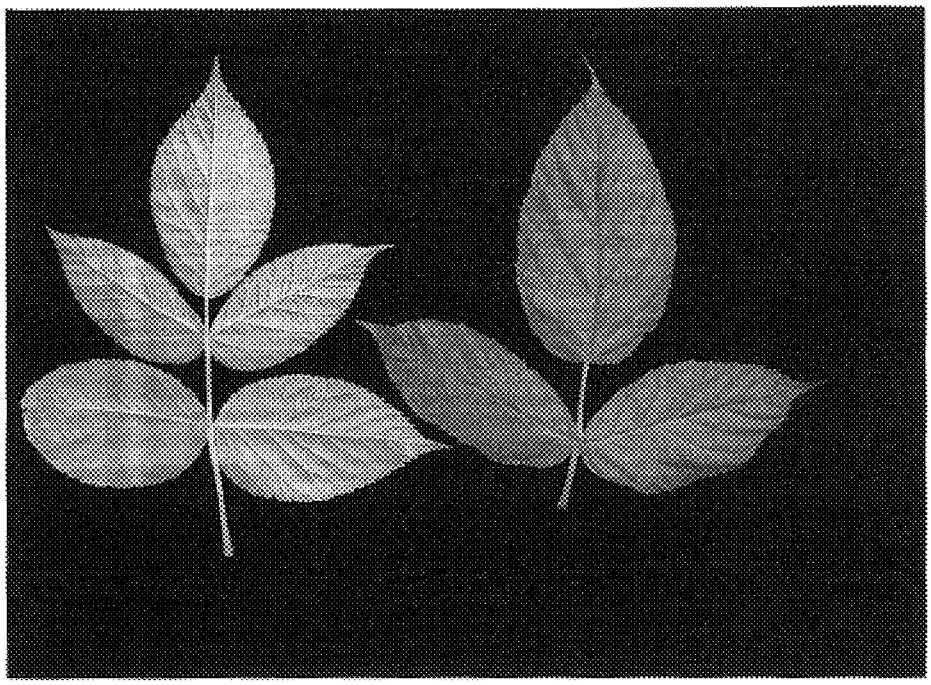
FIG. 2 is a photograph of 'Driscoll Francesca' primocane leaves showing upper and lower leaf surfaces.
Figure 3:
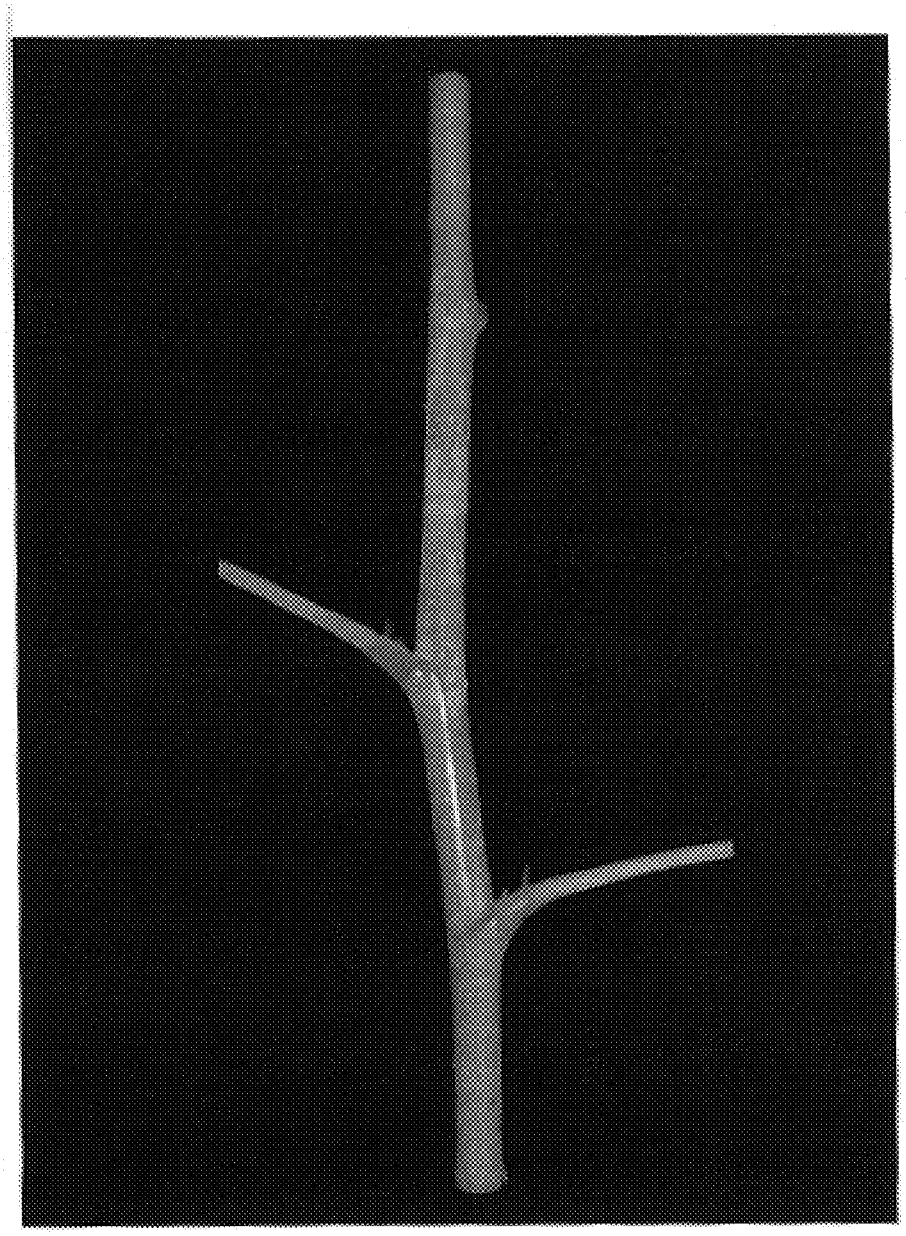
FIG. 3 is a photograph of 'Driscoll Francesca' primocane shoot.

The following detailed description of the new raspberry cultivar, 'Driscoll Francesca', is based upon observations taken of 7 to 17 month old plants and fruit grown in Watsonville, Calif. between 2001 and 2002, and is believed to apply to plants of the 'Driscoll Francesca' cultivar grown in similar conditions of soil and climate elsewhere.

Throughout this specification, color names beginning with a small letter signify that the name of the color, as used in common speech, is aptly descriptive. Color data followed by an alphanumeric code designates the color according to The R.H.S. Colour Chart published by The Royal Horticultural Society of London, England. Color designations, color descriptions, and other phenotypical descriptions may deviate from the stated values and descriptions depending upon variation in environmental, seasonal, climatic and cultural conditions.

Table 1 provides information on the plant and fruit characteristics of the new cultivar 'Driscoll Francesca' compared with characteristics of the unpatented raspberry cultivar 'Heritage'. Observations of the cultivars were taken under similar conditions.

The new variety is particularly characterized and distinguished from other cultivars by its fruit firmness, fruit structure, yield, and flavor.

The fruit color of 'Driscoll Francesca' is a medium red at harvest but darkens after harvest to a deeper color. Fruit of 'Driscoll Francesca' separates easily from the receptacle and is of good firmness at harvest. The fruit of 'Driscoll Francesca' is very consistent in size and shape throughout the harvest period. The average plant height is about 180 cm and the average plant spread is about 80 cm. The prickle color is 187A. The pedicel color is 144A. The sepal color is also 144A.

The reproductive organs of 'Driscoll Francesca' are variable. The pigmentation color of both surfaces of the petals is 155D and there are five petals per flower. The style pigmentation color is 157D, the average number of styles per flower is about 99, the anther pigmentation color is 155D, and the average number of anthers per flower is about 108. The color of the seeds of 'Driscoll Francesca' is 161A, the average seed weight is about 1.4 mg, and there are an average of about 101 seeds per fruit.

The primocane and floricane yields of 'Driscoll Francesca' are high relative to the variety 'Heritage'.

'Driscoll Francesca' is distinguishable from its pollen parent, selection 'Isabel', by producing fruit of consistent shape and good firmness. The new cultivar is distinguished from its seed parent, selection 'Tola', by having better flavor.

4.1 DISEASE AND STRESS RESISTANCE

Resistance is unknown to powdery mildew. Cold tolerance of the new cultivar has not been established. Post harvest fruit rot resistance is good in comparison over many selections and varieties.

TABLE I

PLANT CHARACTERISTICS OF 'DRISCOLL FRANCESCA'

| | Driscoll Francesca | Heritage |
|---|---|---|
| General | | |
| Plant size | Medium | Large |
| Growth habit | Semi-Erect | Erect |
| Productivity | High | Medium |
| Self-fruitfulness | Self-fruitful | Self-fruitful |
| Time of bud burst | Medium | Late |
| Primocane fruiting | | |
| Percent of cane length flowering as primocane | 30–50 | 20–40 |
| Percent of total yield | 40 | 53 |
| Primocanes | | |
| Number of young shoots | | Medium |
| Young shoot pigmentation | Weak | Medium |
| Length (cm) | 212 | 196 |
| Time of shoot emergence | Medium | Very late |
| Glaucosity (waxy bloom) | Strong | Weak |
| Strength | Medium | Medium |
| Cane cross section (from mid cane of primocane) | Rounded to angular | Rounded |
| Dormant cane color | purple mainly with brown | brown to purple brown |
| Prickles | | |
| Pigmentation | brown to purple | green-brownish to green |
| Density on young shoots | medium | Dense |
| Attitude of tip | Downward | Downward |
| Size: Length (base to tip) at 1 m height at the end of season (mm) | 1 | 2.3 |
| Texture | smooth | Rigid |
| Presence and Distribution on Petioles | Present: irregularly | Present irregularly distributed |
| Pubescence on canes | Absent | Absent |
| Internodal distance (cm) (at central ⅓ of cane) | 4.9 | 5.3 |
| LEAVES | | |
| Arrangement | Compound | Compound |
| Relief between veins | Weak | Very weak |

TABLE I-continued

PLANT CHARACTERISTICS OF 'DRISCOLL FRANCESCA'

| | Driscoll Francesca | Heritage |
|---|---|---|
| Number of leaflets | Sometimes 3, somtimes 5 | Sometimes 3, sometimes 5 |
| Overlapping of lateral leaflets | Free to touching | Free to touching |
| Glossiness | Medium | Medium |
| Lateral leaflet: length of stalket (lower pair) | Very short | Very short |
| Terminal leaflet | | |
| Length (cm) | 11.4 | 14.6 |
| Width (cm) | 8 | 7.8 |
| Shape | Ovate | Ovate |
| Tip | Acuminate | Acuminate |
| Base | Cordate | Acute to rounded |
| Margin | Doubly serrate | Doubly serrate |
| Lateral leaflets (basal pair) | | |
| Length (cm) | 10.4 | 14.7 |
| Width (cm) | 6.6 | 8.6 |
| Orientation | Opposite | Opposite |
| Shape | Ovate | Ovate |
| Tip | Acuminate | Acuminate |
| Base | Round | Oblique |
| Margin | Doubly serrate | Doubly serrate |
| Rachis length between terminal leaflet and adjacent Lateral leaflets (cm) | 3.6 | 1.5 |
| Color | | |
| Face | 147A | 147A |
| Underside | 148B | 148B |
| Petiole length (cm) | 4.5 | 7.7 |
| Stipule orientation | Erect | Erect |
| FLOWERS | | |
| Flowering period | | |
| Primocane | 15 weeks, Early May mid September | 19 weeks, Late May Late September |
| Floricane | 12 weeks, Late March to Late June | 10 weeks, Late March to mid June |
| Flower diameter (cm) | 2.0 | 1.8 |
| Petal | | |
| Length (cm) | 0.8 | 0.8 |
| Width (cm) | 0.4 | 0.3 |
| Pedicel coloration | Present, medium intensity | Present, strong intensity |
| FRUIT | | |
| Harvest season | | |
| Primocane | Mid July–early October | Early July–early November |
| Floricane | Mid May–late July | Late May–late July |
| Fruiting Lateral | | |
| Length (4th lateral from tip) (cm) | 61.5 | 49.8 |
| Number of fruit per lateral | 18 | 20.3 |

TABLE I-continued

PLANT CHARACTERISTICS OF 'DRISCOLL FRANCESCA'

| | Driscoll Francesca | Heritage |
|---|---|---|
| Color | | |
| Immature | 44A | 42C |
| Maturing | 46A | 46A |
| Mature Fruit | | |
| Glossiness | Weak | Medium |
| Shape | Ovate | Ovate |
| Dimensions | | |
| Size | Medium | Small |
| Length (mm) | 22 | 17 |
| Width (mm) | 21 | 18 |
| Length: width | 1.05 | 0.94 |
| Weight (g/Fruit) | | |
| Primocane | 4.2 | 3.1 |
| Floricane | 3.7 | 2.3 |
| Soluble solids (%) | 11.3 | 10.8 |
| Titratable acidity (% as citric acid) | 1.41 | 1.58 |
| Seed weight (mg) | 2.8 | 1.5 |
| Number druplets/fruit | 101 | 72 |
| Adherence to plug | Medium | Medium |
| Firmness | Medium | Firm |
| Yield | High | Medium |

4.2 NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531–5). Using a variety of oligonucleotide primers, alone or in combination, RAPD analysis of Driscoll Francesca and Heritage yielded DNA fragment patterns that uniquely distinguish each of these genetically distinct genotypes.

We claim:

1. A new and distinctive cultivar of raspberry plant, substantially as shown and described.

* * * * *